United States Patent
Umayahara et al.

(10) Patent No.: US 11,069,204 B2
(45) Date of Patent: Jul. 20, 2021

(54) ENERGY GENERATION SYSTEM USING BIOMASS AND METHOD OF CONTROLLING THE SAME

(71) Applicant: TOYOTA JIDOSHA KABUSHIKI KAISHA, Toyota (JP)

(72) Inventors: Kenji Umayahara, Miyoshi (JP); Shigeki Takaiwa, Toyota (JP); Masahiro Yamakawa, Toyota (JP); Hideshi Mizutani, Toyota (JP); Takao Ozawa, Toyota (JP); Shigeyuki Suzuki, Nagoya (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 34 days.

(21) Appl. No.: 16/552,337

(22) Filed: Aug. 27, 2019

(65) Prior Publication Data
US 2020/0082681 A1 Mar. 12, 2020

(30) Foreign Application Priority Data
Sep. 7, 2018 (JP) .............................. JP2018-167782

(51) Int. Cl.
*G08B 5/36* (2006.01)
*C01B 3/00* (2006.01)
(Continued)

(52) U.S. Cl.
CPC .............. *G08B 5/36* (2013.01); *C01B 3/0094* (2013.01); *C12P 5/023* (2013.01); *H01M 8/0612* (2013.01)

(58) Field of Classification Search
CPC ......... G08B 5/36; C01B 3/0094; C12P 5/023; C12P 3/00; H01M 8/0612; Y02E 60/50;
(Continued)

(56) References Cited

U.S. PATENT DOCUMENTS

| 5,965,858 A | 10/1999 | Suzuki et al. |
| 2007/0264697 A1 | 11/2007 | Taguchi et al. |
| 2019/0280485 A1* | 9/2019 | Kishi .................. C10L 1/02 |

FOREIGN PATENT DOCUMENTS

| CN | 1149346 A | 5/1997 |
| CN | 1968764 A | 5/2007 |
| JP | 2005-052692 | 3/2005 |

OTHER PUBLICATIONS

Zhang, Minglong et al., "Domestic and International Innovation Information in the Energy Sector," Intellectual Property Publishing House, Sep. 30, 2016, pp. 137-138.
(Continued)

*Primary Examiner* — Toan N Pham
*Assistant Examiner* — Rajsheed O Black-Childress
(74) *Attorney, Agent, or Firm* — Finnegan, Henderson, Farabow, Garrett & Dunner, LLP (57) ABSTRACT

An energy generation system using biomass includes a first information generation unit that generates the first information indicating that a distributor handling food has disposed of food waste biomass, an energy generation device that generates energy and the like using biomass collected from the distributor, a second information generation unit that generates the second information indicating that energy and the like have been generated using biomass collected from the distributor, a third information generation unit that obtains the first information and the second information and generates the third information indicating generation of at least one of energy and energy sources by collecting biomass disposed by the distributor, and a display unit that displays the third information generated by the third information generation unit.

5 Claims, 5 Drawing Sheets

(51) Int. Cl.
*C12P 5/02* (2006.01)
*H01M 8/0612* (2016.01)

(58) Field of Classification Search
CPC ........ Y02E 50/30; Y02P 20/59; Y02P 20/133;
Y02P 20/10; C10L 3/08; C10L 3/00
See application file for complete search history.

(56) References Cited

OTHER PUBLICATIONS

Ju, Naihu, "Handbook of Enzyme Engineering," China Light Industry Press, Aug. 2011, p. 764.

* cited by examiner

| | WASTE BIOMASS AMOUNT | POWER CONSUMPTION | BIOMASS-DERIVED POWER CONSUMPTION | PROPORTION OF BIOMASS-DERIVED POWER CONSUMPTION |
|---|---|---|---|---|
| DISTRIBUTOR 220a | a1 | b1 | c1 | c1／b1 |
| DISTRIBUTOR 220b | a2 | b2 | c2 | c2／b2 |
| DISTRIBUTOR 220c | a3 | b3 | c3 | c3／b3 |

ENERGY GENERATION SYSTEM USING BIOMASS AND METHOD OF CONTROLLING THE SAME

CROSS-REFERENCE TO RELATED APPLICATION

This application claims priority to Japanese Patent Application No. 2018-167782, filed Sep. 7, 2018, the disclosure of which is incorporated by reference herein in its entirety.

BACKGROUND

Field

The present disclosure relates to an energy generation system using biomass and a method of controlling an energy generation system using biomass.

Related Art

Conventionally, there is proposed a processing system for generating energy gas containing hydrogen and methane using biomass including plants, animal products, seafood products, or waste thereof (see Patent Literature 1, for example).

Patent Literature 1: JP 2005-52692A

However, a sequential flow from the collection of biomass to the generation of energy and the supply of generated energy has not been considered sufficiently, and there has been demanded further promotion of the use of biomass as a system related to energy generation using biomass.

SUMMARY

One aspect of the disclosure provides an energy generation system using biomass. The energy generation system includes a first information generation unit that generates first information indicating that a distributor handling food has disposed of food waste biomass, an energy generation device that generates at least one of energy and energy sources using biomass collected from the distributor, a second information generation unit that generates second information indicating that at least one of energy and energy sources have been generated using biomass collected from the distributor, a third information generation unit that obtains the first information from the first information generation unit and the second information from the second information generation unit, and generates third information indicating generation of at least one of energy and energy sources by collecting biomass disposed by the distributor, and a display unit that displays the third information generated by the third information generation unit.

DETAILED DESCRIPTION

Figure 1:
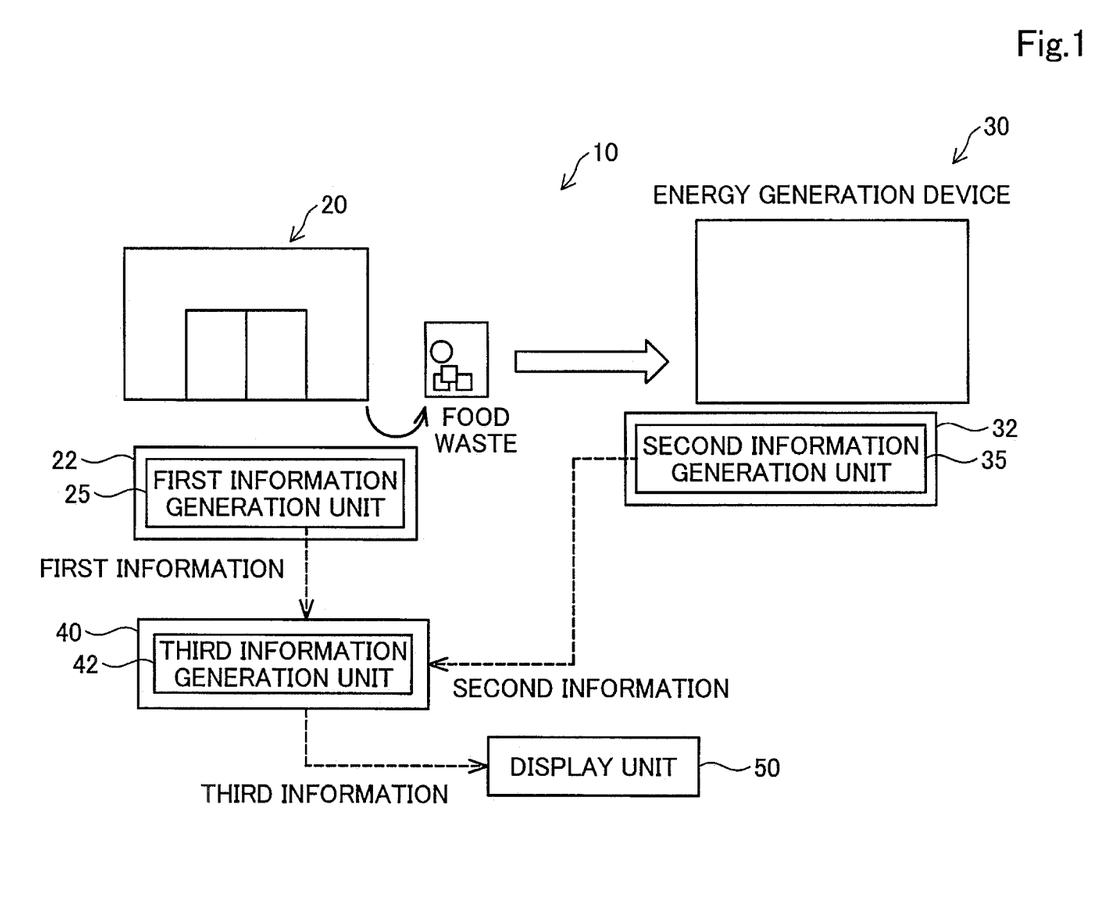
FIG. 1 is an explanatory diagram illustrating a schematic configuration of an energy generation system.

A. First Embodiment (A-1) Entire Configuration of System:

FIG. 1 is an explanatory diagram illustrating a schematic configuration of an energy generation system 10 as a first embodiment of the disclosure. The energy generation system 10 of the first embodiment is a system for generating energy using biomass. The energy generation system 10 includes a distributor 20, an energy generation device 30, a first controller 22, a second controller 32, a third controller 40, and a display unit 50.

The distributor 20 is a distributor handling food where food waste occurs. The distributor 20 may be a food retailer such as a convenience store and a supermarket, a restaurant, a hotel, a hospital, or a composite facility including a plurality of them, for example.

The energy generation device 30 is a device that generates at least one of energy and energy sources (hereinafter, energy and energy sources are also referred to collectively as energy and the like) using food waste biomass collected from the distributor 20. The energy generation device 30 may be a device that generates methane as energy sources from biomass by methane fermentation using microorganisms, or a device that modifies obtained methane and generates hydrogen as energy sources, for example. Moreover, the energy generation device 30 may be a device that generates hydrogen as energy sources from biomass by hydrogen fermentation using microorganisms, or a device that uses organic acid as a byproduct of hydrogen fermentation for methane fermentation and further generates methane as energy sources. Moreover, the energy generation device 30 may be a device that is provided with a fuel cell generating power using hydrogen and performs power generation using hydrogen generated in the above-described manner to generate power energy.

Each of the first controller 22, the second controller 32, and the third controller 40 is configured as a logical circuit with a microcomputer as a center. In detail, each of them includes a CPU performing arithmetic operation in accordance with preset control programs, a ROM preliminarily storing control programs, control data, and the like necessary for various kinds of arithmetic operation by the CPU, a RAM for temporarily reading or writing of various kinds of data necessary for various kinds of arithmetic operation by the CPU, and an input/output port for input and output of various signals.

The first controller 22 is a control device that is provided in a facility such as a convenience store as the distributor 20 and performs control related to distribution management of food that is the merchandise of the distributor 20. The first controller 22 includes at least a first information generation unit 25 as a functional block. The first information generation unit 25 performs control related to disposal and collection of expired merchandises and the like, and generates the first information indicating that the distributor 20 has disposed of biomass as food waste. In the first embodiment, the first information includes the first identification information for association with the second information generated by the second controller 32 described later. The first identification information may be, for example, information for identifying which collection operation has been performed by the distributor 20 to collect biomass related to the first information. The generation of the first information will be described later in detail.

The second controller 32 is a control device that is provided in the energy generation device 30 and performs control related to the operation of receiving biomass collected from the distributor 20 and the operation of using collected biomass for processing of generating energy and the like. The second controller 32 includes at least a second information generation unit 35 as a functional block. The second information generation unit 35 generates the second information indicating that energy and the like have been generated using biomass collected from the distributor 20. In the first embodiment, the second information includes the second identification information for association with the above-described first information generated by the first controller 22. The second identification information may be, for example, information for identifying which distributor has disposed of biomass related to the second information and which collection operation has been performed to collect such biomass. The generation of the second information will be described later in detail.

The third controller 40 is connected to the first controller 22 and the second controller 32 wiredly or wirelessly to receive the first information from the first controller 22 and the second information from the second controller 32. In the first embodiment, the third controller 40 is connected to the first controller 22 and the second controller 32 through the Internet. Then, once the first information is generated, it is transmitted automatically from the first controller 22 to the third controller 30. Once the second information is generated, it is transmitted automatically from the second controller 32 to the third controller 40. The third controller 40 may be provided in a facility such as a convenience store as the distributor 20.

The third controller 40 includes at least a third information generation unit 42 as a functional block. The third information generation unit 42 obtains the first information and the second information and generates the third information indicating generation of energy and the like by collecting biomass disposed by the distributor 20. In the first embodiment, the first information includes the first identification information, and the second information includes the second identification information, as described above. Thus, the third information generation unit 42 uses the correspondence relation between the first identification information and the second identification information to determine whether the obtained first information and second information are related to the same biomass subjected to a sequential operation of disposal and collection, and generates the third information using the first information and the second information related to the same biomass. The generation of the third information will be described later in detail.

The display unit 50 is a device that displays the third information generated by the third information generation unit 42. The display unit 50 is not particularly limited as long as it allows display of the third information. For example, the display unit 50 may be a display device provided in a facility such as a convenience store as the distributor 20. Alternatively, the display unit 50 may be a display unit that is provided in a vehicle of the distributor 20 to be visible from the outside of the vehicle. Moreover, the display unit 50 may be an information terminal for displaying the third information disclosed on a homepage of the distributor 20 or an information terminal for displaying the third information as a banner advertisement, for example, on a movie distribution site and the like on the Internet. Such an information terminal may include, for example, a personal computer, a tablet, a cellular phone, and the like. Moreover, the display unit 50 may be a television receiver for displaying the third information as a television commercial. The display unit 50 may display the third information so as to provide the third information for unspecified large number of public.

Figure 2:
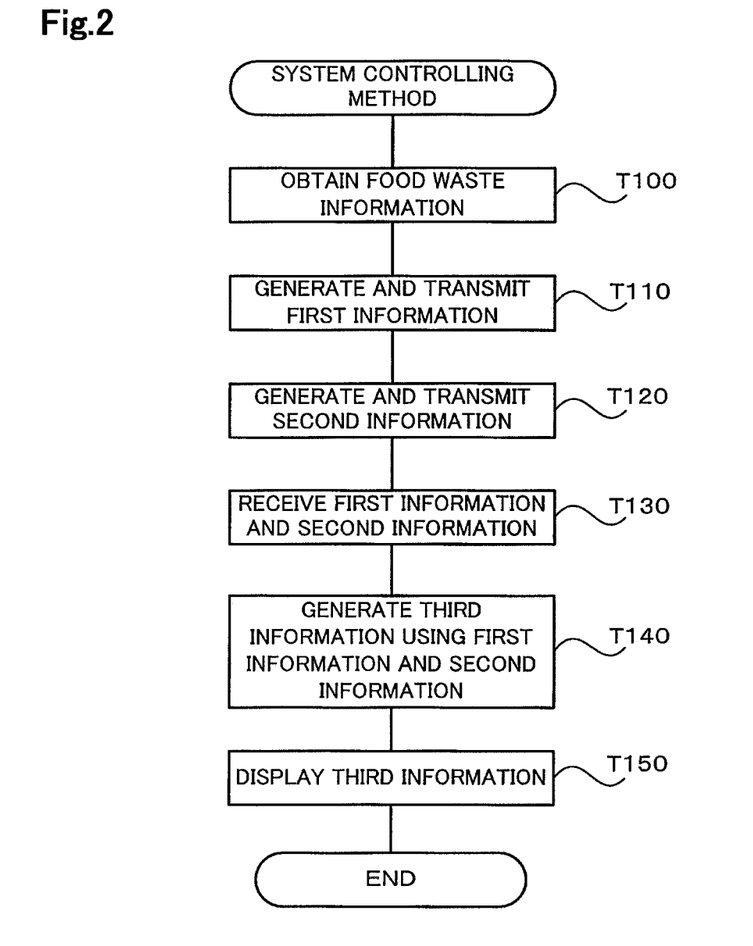
FIG. 2 is a flowchart of a method of controlling an energy generation system.

(A-2) Method of Controlling System:

FIG. 2 is a flowchart illustrating a method of controlling the energy generation system 10 of the first embodiment. First, the CPU of the first controller 22 obtains food waste information (Step T100). The food waste information includes information indicating the kind of waste food. An operator in the distributor 20 reads a barcode of a waste merchandise with a device including the first controller 22 to perform Step T100, for example. The input from a barcode reader connected to the above-described device including the first controller 22 allows the CPU of the first controller 22 to identify the kind of merchandise to be disposed of. Moreover, the storage unit in the first controller 22 may store a rough value of an amount of energy and the like obtained when each merchandise is used as biomass for generation of energy and the like. In this manner, the CPU of the first controller 22 to which barcode reading signals have been, input refers to the storage unit to find an amount of energy and the like obtained from merchandises to be disposed of. Therefore, the food waste information obtained at Step T100 may include information indicating the fact that a merchandise whose barcode has been read is disposed of and the amount of energy and the like obtained from the merchandise.

The distributor 20 accumulates biomass to be disposed of until a vehicle for carrying out biomass arrives next time, for example. Until then, the CPU of the first controller 22 repeatedly obtains food waste information at Step T100, so that the food waste information is accumulated. Then, once the carry-out by a biomass carrying out vehicle is detected, the CPU of the first controller 22 generates the first information using food waste information accumulated so far and transmits the generated first information to the third controller 40 (Step T110). In the first embodiment, a facility such as a convenience store as the distributor 20 has a sensor detecting a biomass carrying out vehicle, and detection signals of the sensor are transmitted to the first controller 22, thus detecting the carry-out.

As described above, the first identification information includes at least information indicating that the distributor 20 has disposed of biomass, and further includes the first identification information for association with the second information generated by the second controller 32. The first identification information may be, for example, a date and time when biomass in the distributor 20 is collected, and more concretely a date and time when the carry-out by a biomass carrying out vehicle is detected. Moreover, if the energy generation device 30 collects biomass disposed of by a plurality of distributors 20 to generate energy and the like, the first information may include information indicating the distributor having disposed of biomass related to the first information. The information indicating a distributor having disposed of biomass is also referred to as the third identification information. As described above, the first information may further include information indicating an amount of energy and the like obtained from waste biomass.

Once the biomass is carried out from the distributor 20 and the energy generation device 30 detects the carry-in of biomass by a biomass carrying out vehicle, the CPU of the second controller 32 generates the second information and transmits it to the third controller 40 (Step T120). In the first embodiment, the energy generation device 30 includes a sensor detecting a biomass carrying out vehicle. The detection signals of the sensor are transmitted to the second controller 32, thus detecting the carry-in.

As described above, the second information includes at least information indicating that energy and the like have been generated using biomass collected from the distributor 20, and further includes the second identification information for association with the first information generated by the first controller 22. The second identification information may be, for example, a date and time when the energy generation device 30 receives biomass, and more concretely a data and time when the carry-in by a biomass carrying out vehicle is detected. Moreover, if the energy generation device 30 collects biomass disposed of by a plurality of distributors 20 to generate energy and the like, the second identification information may include information indicating the distributor having disposed of biomass related to the second information. The information indicating a distributor having disposed of biomass is also referred to as the fourth identification information. In this case, for example, the biomass carrying out vehicle may transmit signals for identifying the distributor 20 having disposed of biomass, so that a receiver of the energy generation device 30 receives the signals and transmits them to the second controller 32.

After the first controller 22 transmits the first information and the second controller 32 transmits the second information, the third controller 40 receives the first information and the second information (Step T130). Then, the CPU of the third controller 40 generates the third information using the first information and the second information (Step T140). As described above, the first information includes the first identification information, and the second information includes the second identification information. Thus, the third information generation unit 42 uses the correspondence relation between the first identification information and the second identification information to recognize that the obtained first information and second information are related to the same biomass subjected to a sequential operation of disposal and collection and then generate the third information.

As described above, the third information includes at least information indicating generation of energy and the like by collecting biomass disposed by the distributor 20. Then, if the first information includes information indicating an amount of energy and the like obtained from biomass disposed of by the distributor 20, the third information may further include information indicating an amount of energy and the like generated using biomass collected from the distributor 20.

Once the CPU of the third controller 40 generates the third information, the third controller 40 transmits the generated third information to the display unit 50 so that the display unit 50 displays the third information (Step T150). For example, if the display unit 50 is the above-described display device provided in a facility of the distributor 20, the third controller 40 may transmit instruction signals for displaying the generated third information to the above-described display device wiredly or wirelessly. Alternatively, the third controller 40 may access a server storing information to be disclosed on a homepage of the distributor 20 or a server storing information to be distributed as a banner advertisement or a television commercial, for example, through the Internet, and transmit the third information to such a server.

The concrete contents displayed by the display unit 50 are not particularly limited as long as the third information is displayed. For example, the display unit 50 may display the fact that the distributor 20 collects waste biomass to generate energy and the like, or display whether the energy and the like are generated currently. If the third information generated by the third information generation unit 42 includes an amount of generated energy and the like, as described above, the display unit 50 may display the amount of generated energy and the like in addition to the above-described fact that the energy and the like are generated. The contents displayed by the display unit 50 may be updated every time the third information generation unit 42 newly generates the third information, for example. Alternatively, the contents displayed by the display unit 50 may be updated with predetermined intervals of time, for example, every day at every predetermined time, for example. From the viewpoint of displaying information indicating that the distributor 20 collects waste biomass to generate energy and the like, the display of the third information by the display unit 50 or update of the third information to be displayed on the display unit 50 may be performed continuously. Here, "performed continuously" does not necessarily indicate "performed constantly" or "performed with same intervals", but it indicates "performed repeatedly".

The energy generation system 10 of the first embodiment configured in the above-described manner displays the third information indicating generation of energy and the like by collecting biomass disposed by the distributor 20. Thus, it is possible to effectively utilize biomass and further promote the use of biomass. For example, even if the generation of energy and the like using biomass costs more than the case in which food waste is not utilized as biomass and is disposed of as it is, social evaluation of the distributor 20 is improved, which promotes the use of biomass. Especially if the third information includes information indicating at least one of an amount of energy and an amount of energy sources generated using biomass collected from the distributor 20, it is possible to display the fact that the distributor 20 utilizes waste biomass in a more concrete manner.

FIG. 1 illustrates a single facility such as a convenience store as the distributor 20. However, the embodiment may have a different configuration. For example, the distributor 20 may be a collective of facilities such as a plurality of convenience stores belonging to a same group in a form of franchise or the like or a collective of facilities such as a plurality of retail stores run by a same management subject. In this case, the distributor 20 having a plurality of facilities as a whole may generate and display the third information. For example, it is possible to display the third information indicating the total amount of energy and the like generated using biomass disposed of by each of a plurality of facilities of the distributor 20. Here, the number of energy generation device 30 does not need to be one for the plurality of facilities. A plurality of energy generation devices 30 may be used in such a way that a different energy generation device 30 is used for each facility, for example. In this case, each energy generation device 30 may transmit the second information to the third controller 40. Here, the third information may be displayed for each facility, or for the distributor 20 as a whole with distinction among facilities, or as the collective result of the distributor 20 as a whole.

B. Second Embodiment

Figure 3:
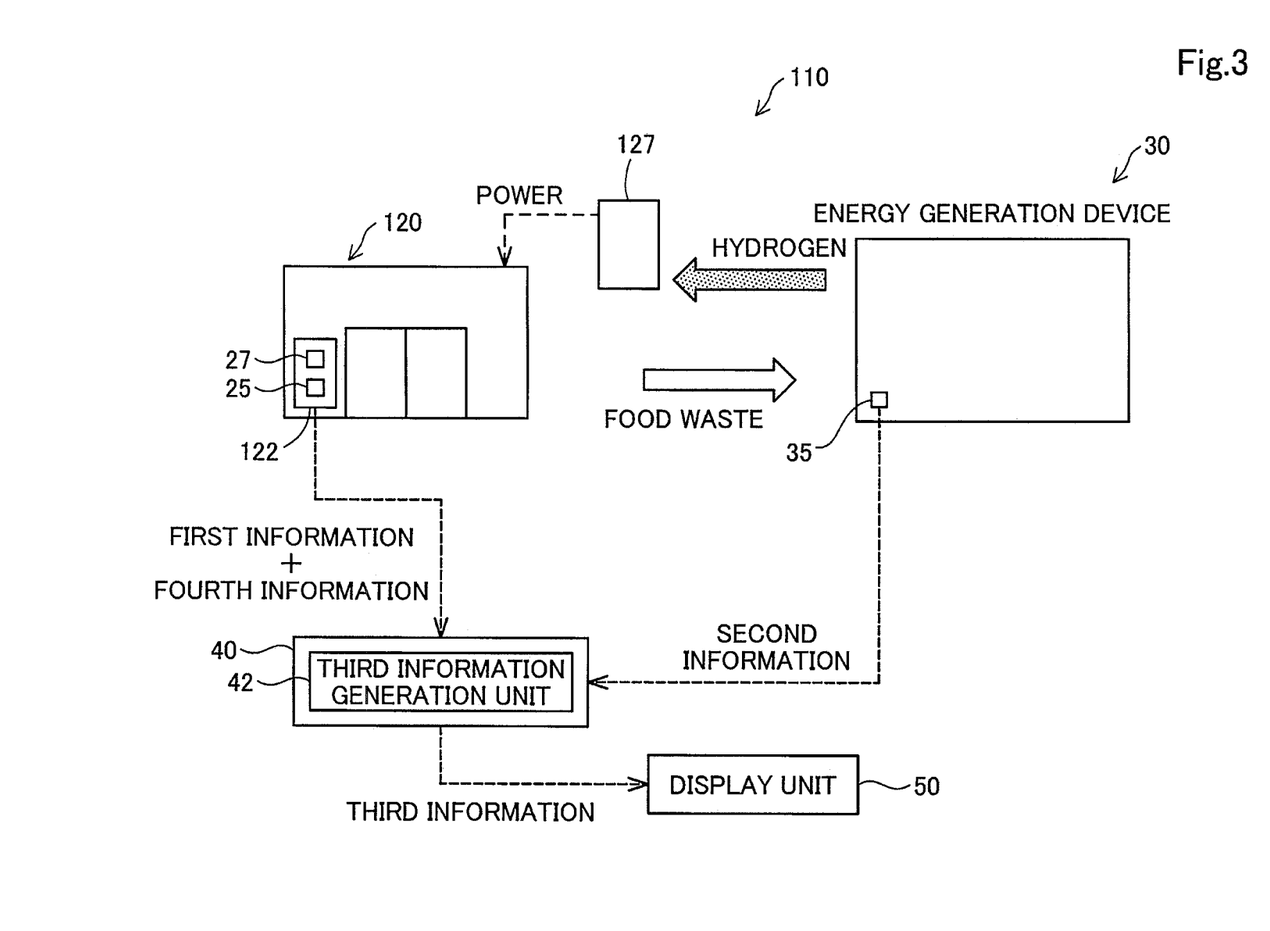
FIG. 3 is an explanatory diagram illustrating a schematic configuration of an energy generation system.

FIG. 3 is an explanatory diagram illustrating a schematic configuration of an energy generation system 110 as a second embodiment of the disclosure. In the energy generation system 110 of the second embodiment, the parts same as the energy generation system 10 of the first embodiment are represented with the same referential symbols, and the detailed description thereof is omitted.

In the energy generation system 110 of the second embodiment, the distributor 120 uses energy and the like generated by the energy generation device 30 using biomass disposed of by the distributor 120. To be more specific, the distributor 120 has a fuel cell 127 that is a power generation device generating power using hydrogen and oxygen. Then, the distributor 120 receives supply of hydrogen that is energy sources, as energy and the like generated by the energy generation device 30, so that the fuel cell 127 generates power using the hydrogen, thus covering at least apart of power to be consumed by the distributor 120.

In such a case, the third information may further include information indicating that the distributor 120 uses at least one of energy and energy sources generated using biomass. In the second embodiment, the distributor 20 includes a first controller 122 instead of the first controller 22. The first controller 122 includes a fourth information generation unit 27 in addition to the first information generation unit 25. The fourth information generation unit 27 generates, as the fourth information, information indicating that the distributor 120 uses energy and the like generated using biomass. For example, if the fuel cell 127 generates power using hydrogen supplied from the energy generation device 30, signals detecting power generation of the fuel cell 127 are input to the fourth information generation unit 27, which allows the fourth information generation unit 27 to generate the above-described fourth information. After the first information and the fourth information are generated in the above-described manner, the first controller 122 transmits the first information and the fourth information to the third controller 40. As a result, the third information generation unit 42 generates the third information including the fourth information, and the display unit 50 displays the third information including the fourth information.

Also in such a configuration, it is possible to obtain the same effects as the first embodiment. Furthermore, the distributor 120 uses energy and the like derived from waste biomass, which contributes to reduction of an amount of carbon dioxide occurred by the activity of the distributor 120 itself. Moreover, with the display of the third information including information indicating that the distributor 120 uses energy and the like generated using biomass, it is possible to further improve social evaluation of the distributor 120 and thus further enhance motivation for the use of biomass.

In FIG. 3, the distributor 120 has the fuel cell 127, and receives supply of hydrogen as energy and the like generated by the energy generation device 30. However, the embodiment may have a different configuration. For example, if the energy generation device 30 generates power as energy and the like, the distributor 120 may receive supply of power from the energy generation device 30 and use it.

In FIG. 3, the distributor 120 uses hydrogen supplied from the energy generation device 30 to obtain power to be consumed by the distributor 120 itself. However, it is also possible to provide the supplied hydrogen with or without charge. For example, the distributor 120 may have both a facility for handling food and a hydrogen station for providing hydrogen for fuel cell vehicles and the like. In such a case, hydrogen supplied from the energy generation device 30 may be sold at the hydrogen station.

C. Third Embodiment

Figure 4:
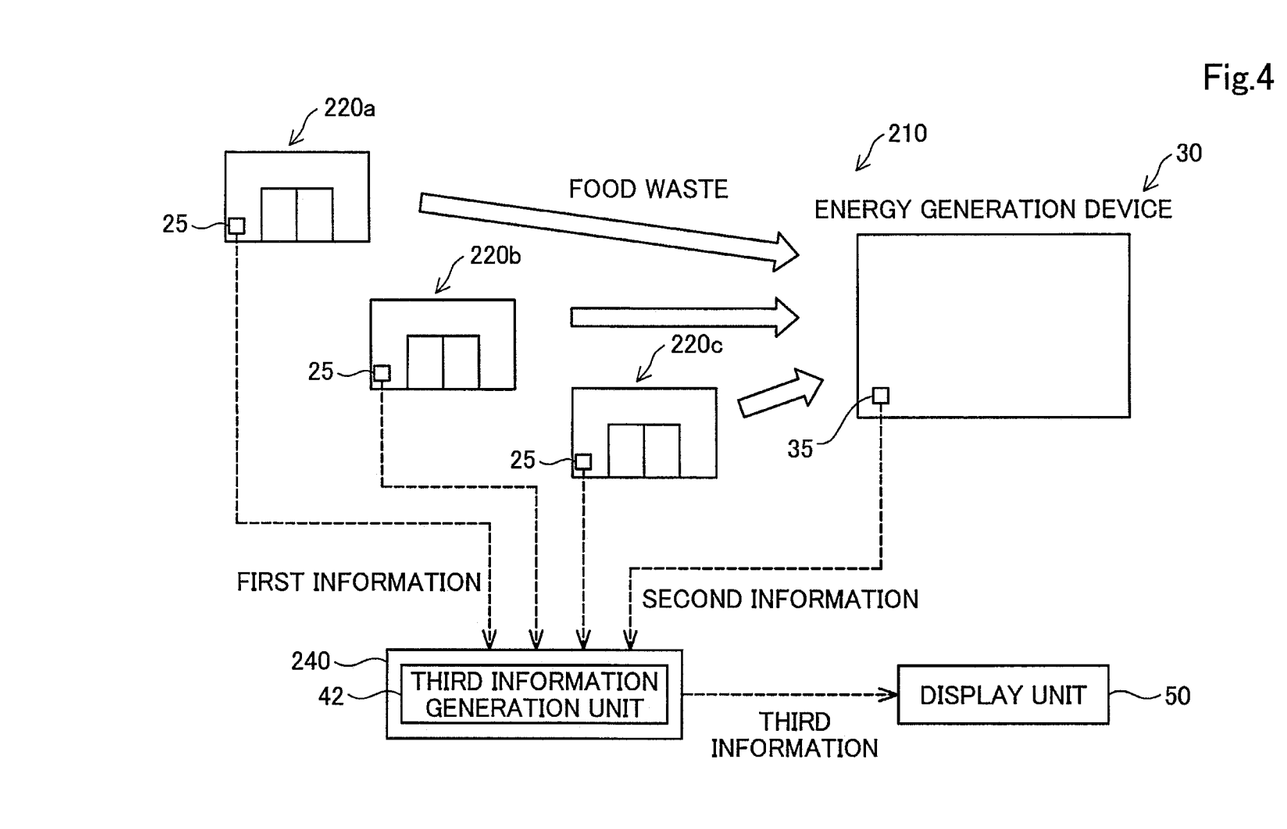
FIG. 4 is an explanatory diagram illustrating a schematic configuration of an energy generation system.

FIG. 4 is an explanatory diagram illustrating a schematic configuration of an energy generation system 210 as a third embodiment of the disclosure. In the energy generation system 210 of the third embodiment, the parts same as the energy generation system 10 of the first embodiment are represented with the same referential symbols, and the detailed description thereof is omitted.

In the energy generation system 210 of the third embodiment, a plurality of distributors 220a, 220b, 220c exist. In FIG. 4, the number of distributors is three. However, two or more distributors may exist. Each of the distributors 220a, 220b, 220c may have a plurality of facilities where biomass is disposed of. For example, each of the distributors 220a, 220b, 220c may be a collective of facilities such as a plurality of convenience stores belonging to a same group or a collective of facilities such as a plurality of retail stores run by a same management subject.

In the third embodiment, at least one of the distributors 220a, 220b, 220c uses energy and the like generated by the energy generation device 30. Then, the third information generated by the third information generation unit 42 includes information indicating that at least one of the distributors uses energy and the like generated using biomass. The following describes a configuration as an example in which each distributor uses power generated by the energy generation device 30.

In the third embodiment, each of the distributors 220a, 220b, 220c has the first information generation unit 25. FIG. 4 illustrates the single energy generation device 30 that generates energy and the like from biomass disposed of by the distributors 220a, 220b, 220c. However, a plurality of energy generation devices 30 may be provided, so that each distributor uses a different energy generation device 30. The energy generation system 210 of the third embodiment includes a third controller 240 instead of the third controller 40 of the first embodiment. The third controller 240 includes at least the third information generation unit 42 as a functional block. The third controller 240 may be provided in a third party different from any of the distributors 220a, 220b, 220c.

At Step T130 of FIG. 2, the third controller 240 obtains the first information from the first information generation unit 25 of each of the distributors 220a, 220b, 220c. In the third embodiment, the first information obtained by the third controller 240 from the first information generation unit 25 of each of the distributors 220a, 220b, 220c includes the third identification information indicating distributors having disposed of biomass related to the first information. Moreover, at Step T130 of FIG. 2, the third controller 240 obtains the second information related to biomass disposed of by each of the distributors 220a, 220b, 220c from the second information generation unit 35 of the energy generation device 30. In the third embodiment, the second information generated by the second information generation unit 35 of the energy generation device 30 includes the fourth identification information indicating distributors having disposed of biomass related to the second information. At Step T140 of FIG. 2, the third controller 240 generates the third information regarding the distributors 220a, 220b, 220c while associating the third identification information and the fourth identification information using the above-described first information and second information. At Step T150, the display unit 50 having obtained the third information from the third controller 240 collectively displays the third information generated for each of the distributors 220a, 220b, 220c by the third controller 240.

In the third embodiment, the third information further includes, for each distributor, a waste biomass amount a, a power consumption b, a power consumption c derived from biomass in power consumed by each distributor (hereinafter, referred to as a biomass-derived power consumption c), and a proportion (c/b) of a biomass-derived power consumption c relative to the power consumption b. The waste biomass amount a for each distributor may be found by the following manner, for example. That is, at Step T100, the food waste information obtained by the first controller 22 of each distributor may include information indicating a weight of waste. Then, when the third controller 240 generates the third information at Step T140, the third information generation unit 42 may collect the amount of biomass disposed of by each distributor in a predetermined period of time and find, as a waste biomass amount a included in the third information, a waste biomass amount a1, a2, a3 for each of the distributors 220a, 220b, 220c. To obtain information indicating a weight of waste at Step T100, the storage unit of the first controller 22 may store a weight of each merchandise, for example, so that when each distributor reads barcodes of waste merchandises, the first controller 22 of the distributor refers to the storage unit to find information indicating the weight of the merchandises.

The first information includes information indicating a power consumption of each of the distributors 220a, 220b, 220c in a predetermined period of time, which allows the third information generation unit 42 to obtain the power consumption b. The biomass-derived power consumption c may be a power amount obtained from the energy generation device 30 by each distributor in a predetermined period of time. The first information includes information indicating such a power amount, which allows the third information generation unit 42 to obtain the biomass-derived power consumption c. The third information generation unit 42 of the third embodiment further calculates (c/b) using the power consumption b and the biomass-derived power consumption c and includes the calculation result in the third information.

Figure 5:
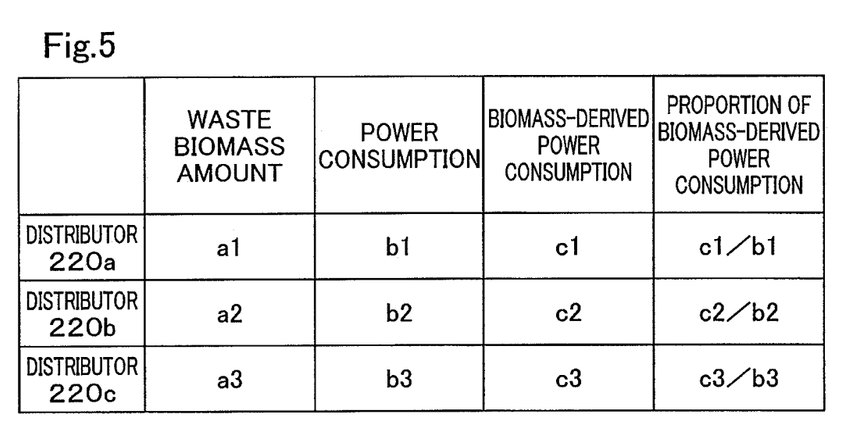
FIG. 5 is an explanatory diagram illustrating an example of third information displayed by a display unit.

FIG. 5 is an explanatory diagram illustrating an example of the third information displayed by the display unit 50 of the third embodiment. FIG. 5 illustrates a list display of the waste biomass amount a, the power consumption b, the biomass-derived power consumption c, and (c/b) for each distributor. FIG. 5 is an example, and the displayed third information may include different kinds of information from FIG. 5.

In such a configuration, it is possible to obtain the same effects as the first embodiment and the second embodiment. The collective display of the third information related to a plurality of distributors allows comparison among other distributors. This, as a result, enhances the motivation of each distributor for the use of biomass and further improves social evaluation of distributors actively utilizing biomass, thus further promoting the use of biomass.

In the third embodiment, the energy generation device 30 generates power as energy, and each distributor uses power generated by the energy generation device 30. However, the embodiment may have a different configuration. For example, similarly to the second embodiment, the energy generation device 30 may generate hydrogen as energy sources, and each distributor performs power generation by a fuel cell using hydrogen generated by the energy generation device 30. In this case, the biomass-derived power consumption c illustrated in FIG. 5 may be a power amount generated using biomass-derived hydrogen supplied to each distributor from the energy generation device 30.

D. Other Embodiments (D1) In the above-described embodiments, the distributor and the energy generation device 30 are positioned separately from each other, and in the third embodiment, the energy generation device 30 uses biomass collected from a plurality of distributors. However, the embodiment may have a different configuration. For example, the energy generation device 30 may be provided for each distributor to be adjacent to the distributor.

(D2) In the above-described embodiments, the first information is generated using food waste information obtained at Step T100 by reading barcodes of waste merchandises. However, the embodiment may have a different configuration. For example, having obtained signals detecting carry-out by a biomass carrying out vehicle, the first controller 22 may generate the first information indicating that biomass has been disposed of. Here, if each distributor has a sensor automatically detecting a weight of biomass to be carried out, the first controller 22 may obtain a detection value of the sensor to include the information indicating the weight of biomass in the first information to be generated. Furthermore, if the first controller 22 stores a rough value of an amount of energy and the like generated per unit weight of biomass, it is possible to use the rough value to calculate a rough value of energy and the like generated from waste biomass. In this manner, the first information and the third information may include information indicating an amount of energy and the like generated from waste biomass.

The weight of biomass used for energy generation may be detected when biomass is carried into the energy generation device 30, instead of when biomass is carried out from each distributor. Here, if the second controller 32 stores a rough value of an amount of energy and the like generated per unit weight of biomass, for example, the second controller 32 may calculate a rough value of energy and the like generated from waste biomass. In such a case, it is possible to include information indicating an amount of energy and the like generated from waste biomass in the second information and the third information.

(D3) In the above-described embodiments, the first information includes the first identification information, and the second information includes the second identification information. However, the embodiment may have a different configuration. For example, if the correspondence relation is clear between biomass disposed of by a distributor and biomass collected and used for generation of energy and the like by the energy generation device 30, such a case in which the energy generation device 30 is provided for each distributor, it is not necessary to use the first identification information and the second identification information for associating the first information and the second information.

The disclosure is not limited to the above-described embodiments, and may be achieved by various configurations without departing from the scope of the disclosure. For example, the technical features in the embodiments corresponding to the technical features of each aspect in the summary of the disclosure may be appropriately replaced or combined in order to solve a part or all of the above-described problems or achieve a part or all of the above-described effects. Moreover, unless the technical features are explained as necessary in the specification, they may be deleted appropriately. For example, the present disclosure may be implemented as the following aspects.

(1) One aspect of the disclosure provides an energy generation system using biomass. The energy generation system includes a first information generation unit that generates first information indicating that a distributor handling food has disposed of food waste biomass, an energy generation device that generates at least one of energy and energy sources using biomass collected from the distributor, a second information generation unit that generates second information indicating that at least one of energy and energy sources have been generated using biomass collected from the distributor, a third information generation unit that obtains the first information from the first information generation unit and the second information from the second information generation unit, and generates third information indicating generation of at least one of energy and energy sources by collecting biomass disposed by the distributor, and a display unit that displays the third information generated by the third information generation unit. The energy generation system of this aspect displays the third information indicating generation of at least one of energy and energy sources by collecting biomass disposed by the distributor. Thus, it is possible to utilize biomass effectively and further promote the use of biomass.

(2) In the energy generation system of the above-described aspect, the first information and the third information may include information indicating at least one of an amount of energy and an amount of energy sources generated using biomass collected from the distributor. In the energy generation system of this aspect, it is possible to display the fact that the distributor utilizes waste biomass in a more concrete manner.

(3) In the energy generation system of the above-described aspect, the distributor may use at least one of energy and energy sources generated using biomass by the energy generation device, and the third information may include information indicating that the distributor uses at least one of energy and energy sources generated using biomass. In the energy generation system of this aspect, the distributor uses energy and the like generated using biomass by the energy generation device, which contributes to reduction of an amount of carbon dioxide occurred by the activity of the distributor itself. Moreover, with the display of the third information including information indicating that the distributor uses energy and the like generated using biomass and the like, it is possible to further improve social evaluation of the distributor and thus further enhance motivation for the use of biomass.

(4) In the energy generation system of the above-described aspect, a plurality of distributors may exist as the distributor, and the display unit may collectively display the third information generated for each of the distributors. In the energy generation system of this aspect, the collective display of the third information related to a plurality of distributors allows comparison among other distributors. This, as a result, enhances the motivation of each distributor for the use of biomass and further improves social evaluation of distributors actively utilizing biomass, thus further promoting the use of biomass.

(5) In the energy generation system of the above-described aspect, the energy generation device may generate hydrogen as the energy sources. In the energy generation system of this aspect, it is possible to promote the use of hydrogen derived from biomass.

The disclosure may be achieved by various aspects, and may be achieved by the aspects of a method of controlling an energy generation system, a computer program achieving the method of controlling an energy generation system, a non-temporary recording medium storing the computer program, and the like.

What is claimed is:

1. An energy generation system using biomass, comprising:
   a first information generation unit that generates first information indicating that a distributor handling food has disposed of food waste biomass;
   an energy generation device that generates at least one of energy or energy sources using biomass collected from the distributor, wherein the distributor uses at least one of energy or energy sources generated using biomass by the energy generation device;
   a second information generation unit that generates second information indicating that at least one of energy or energy sources have been generated using biomass collected from the distributor;
   a third information generation unit that obtains the first information from the first information generation unit and the second information from the second information generation unit, and generates third information indicating generation of at least one of energy or energy sources by collecting biomass disposed by the distributor, wherein the third information includes:
      information indicating that the distributor uses at least one of energy or energy sources generated using biomass, and
      information indicating a proportion (c/b) of a biomass-derived power consumption c relative to a power consumption b for the distributor; and
   a display unit that displays the third information generated by the third information generation unit.

2. The energy generation system according to claim 1, wherein
   the first information and the third information include information indicating at least one of an amount of energy or an amount of energy sources generated using biomass collected from the distributor.

3. The energy generation system according to claim 1, wherein
   a plurality of distributors exist as the distributor, and
   the display unit collectively displays the third information generated for each of the distributors.

4. The energy generation system according to claim 1, wherein the energy generation device generates hydrogen as the energy sources.

5. A method of controlling an energy generation system using biomass, the method comprising:
   generating first information indicating that a distributor handling food has disposed of food waste biomass, wherein the distributor uses at least one of energy or energy sources generated using biomass;
   generating second information indicating that at least one of energy or energy sources have been generated using biomass collected from the distributor;
   generating, using the first information and the second information, third information indicating generation of at least one of energy or energy sources by collecting biomass disposed by the distributor, wherein the third information includes:
      information indicating that the distributor uses at least one of energy or energy sources generated using biomass, and
      information indicating a proportion (c/b) of a biomass-derived power consumption c relative to a power consumption b for the distributor; and
   displaying the generated third information on a display unit.

* * * * *